(12) United States Patent
Barton et al.

(10) Patent No.: US 8,859,846 B2
(45) Date of Patent: Oct. 14, 2014

(54) DOUBLING OF CHROMOSOMES IN HAPLOID EMBRYOS

(75) Inventors: Joanne E. Barton, Wilmington, DE (US); Sheila E. Maddock, Johnston, IA (US); Xinli E. Wu, Johnston, IA (US); Zuo-Yu Zhao, Johnston, IA (US); Mark E. Williams, Newark, DE (US); Tanveer Hussain, Urbandale, IA (US); William J. Gordon-Kamm, Urbandale, IA (US)

(73) Assignees: E. I. du Pont de Nemours and Company, Wilmington, DE (US); Pioneer Hi-Bred International, Inc., Johnston, IA (US)

( * ) Notice: Subject to any disclaimer, the term of this patent is extended or adjusted under 35 U.S.C. 154(b) by 1832 days.

(21) Appl. No.: 11/532,921

(22) Filed: Sep. 19, 2006

(65) Prior Publication Data

US 2008/0216191 A1 Sep. 4, 2008

Related U.S. Application Data

(60) Provisional application No. 60/718,989, filed on Sep. 21, 2005.

(51) Int. Cl.
*A01H 1/08* (2006.01)
*A01H 4/00* (2006.01)

(52) U.S. Cl.
CPC .................... *A01H 1/08* (2013.01)
USPC ........... 800/275; 800/268; 800/299; 435/424; 435/430.1

(58) Field of Classification Search
USPC .......................... 800/260, 269, 275
See application file for complete search history.

(56) References Cited

U.S. PATENT DOCUMENTS

| | | | |
|---|---|---|---|
| 5,491,084 A * | 2/1996 | Chalfie et al. | 506/10 |
| 2003/0005479 A1 | 1/2003 | Kato | |
| 2004/0210959 A1 | 10/2004 | Armstrong et al. | |
| 2005/0289673 A1 | 12/2005 | Armstrong et al. | |

FOREIGN PATENT DOCUMENTS

| | | |
|---|---|---|
| JP | 09084478 A | 3/1997 |
| WO | 02085104 A2 | 10/2002 |
| WO | 2006128707 A1 | 12/2006 |

OTHER PUBLICATIONS

Wan et al. Theor Appl Genet 77: 889-892, 1989.*
Wan et al. Theor Appl Genet 81: 205-211, 1991.*
Chalyk. Euphytica 79: 13-18, 1994.*
Sood et al. Plant Breeding 122: 493-496, 2003.*
Nedev et al. Colchicine—mediated doubling of corn maternal haploids. 2001. Maize Genetics Cooperation Newsletter. 75:59.*
Barnabas et al., Colchicine, an efficient genome-doubling agent for maize (*Zea mays* L.) microspores cultured in anthero, Plant Cell Reports (1999) 18(10):858-862.
Nedev et al., Colchicine-induced chromosome doubling of maternal haploids with invitro culture, Maize Genetics Cooperation Newsletter (1999) 73:80.
Nedev et al., Colchicine—mediated doubling of corn maternal haploids, Maize Genetics Cooperation Newsletter (2001) 75:59.
Wright, Leslie Jay, Doubled Haploid Production in Barley (*Hordeum vulgare* L.) Using Interspecific Hybridization and Nitrous Oxide Treatment, Dissertation Abstracts International B. The Science and Engineering (1982) pp. 1-52.

* cited by examiner

*Primary Examiner* — David T Fox
*Assistant Examiner* — Jeffrey Bolland

(57) ABSTRACT

Methods for producing doubled haploid corn (*Zea mays*) plants, seeds, and plant cells are provided.

10 Claims, No Drawings

DOUBLING OF CHROMOSOMES IN HAPLOID EMBRYOS

FIELD OF THE INVENTION

The present invention relates to the field of plant breeding and the making of doubled haploid plants.

BACKGROUND OF THE INVENTION

Homozygous plants are basic for product development and commercialization of plants. To obtain homozygous plants requires several generations of self-pollination and segregation analysis. This is an inefficient use of labor and time resources. It would therefore be useful to develop a method to reduce hand pollination steps normally required to obtain a homozygous plant and reduce the amount of time required to obtain a homozygous population of plants. One way to obtain homozygous plants without the need to self-pollinated multiple generations is to produce haploids and then double the chromosomes to form doubled haploids.

SUMMARY OF THE INVENTION

Methods for producing doubled haploid plants, seeds, and plant cells are provided. The methods presented increase the efficiency of the doubled haploid process by increasing the number of doubled haploids obtained and by decreasing the amount of time required to produce the doubled haploids.

DETAILED DESCRIPTION OF THE INVENTION

A haploid plant has a single set (genome) of chromosomes and the reduced number of chromosomes (n) in the haploid plant is equal to that in the gamete.

A diploid plant has two sets (genomes) of chromosomes and the chromosome number (2n) is equal to that in the zygote.

A doubled haploid or doubled haploid plant or cell is one that is developed by the doubling of a haploid set of chromosomes. A plant or seed that is obtained from a doubled haploid plant that is selfed any number of generations may still be identified as a doubled haploid plant. A doubled haploid plant is considered a homozygous plant. A plant is considered to be doubled haploid if it is fertile, even if the entire vegetative part of the plant does not consist of the cells with the doubled set of chromosomes. For example, a plant will be considered a doubled haploid plant if it contains viable gametes, even if it is chimeric.

A "haploid immature embryo" is defined as the embryo formed after one sperm nucleus from a pollen grain fuses with the polar nuclei in the embryo sac to create a triploid (3N) endosperm and before dry down.

A "doubled haploid embryo" is an embryo that has one or more cells that contain 2 sets of homozygous chromosomes.

"Callus" refers to a dedifferentiated proliferating mass of cells or tissue.

The phrases "contacting", "comes in contact with" or "placed in contact with" can be used to mean "direct contact" or "indirect contact". For example, the medium comprising a doubling agent may have direct contact with the haploid cell or the medium comprising the doubling agent may be separated from the haploid cell by filter paper, plant tissues, or other cells thus the doubling agent is transferred through the filter paper or cells to the haploid cell.

The term "medium" includes compounds in liquid, gas, or solid state.

As used herein, the term "plant" includes reference to whole plants, plant organs (e.g., leaves, stems, roots, etc.), seeds and plant cells and progeny of same. "Plant cell", as used herein includes, without limitation, seeds, suspension cultures, embryos, meristematic regions, callus tissue, leaves, roots, shoots, gametophytes, sporophytes, pollen, and microspores. The class of plants which can be used in the methods of provided include both monocotyledonous and dicotyledonous plants.

Provided are methods for 1) identifying haploid embryos at an early stage with high accuracy, 2) chromosomal doubling protocols at an early stage of embryo development, 3) plant generation from early stage embryos. The methods are generally genotype independent, thus extending the scope of plants that can be used to produce doubled haploids. The methods generally produce a high frequency of doubled haploid plants that are fertile.

One method provided comprises obtaining a doubled haploid embryo, seed, or plant by contacting a haploid embryo with a doubling agent and obtaining a doubled haploid embryo, seed, or plant.

Another method provided is obtaining a doubled haploid plant comprising the following steps: a) pollinating ovules, or stigmas, of a plant with pollen from an inducer line, wherein the inducer line has a marker gene that is expressed in embryos and/or endosperm tissue; b) selecting a haploid embryo which does not express a marker gene; c) contacting the haploid embryo with a gas, solution or solid comprising a doubling agent; and d) regenerating that embryo into a doubled haploid plant.

Another method is obtaining a doubled haploid seed comprising the following steps: a) obtaining a haploid seed by pollinating an ovule with an inducer line wherein the ovule comprises a set of maternal chromosomes and wherein the inducer line comprises a set of paternal chromosomes; b) contacting the haploid seed with a medium comprising a doubling agent; c) selecting a doubled haploid seed wherein the doubled haploid seed comprises a triploid endosperm and a doubled haploid embryo. The doubled haploid seed produced by such a method wherein the triploid endosperm comprises two sets of maternal chromosomes and one set of paternal chromosomes, and wherein the doubled haploid embryo has a first and second set of maternal chromosomes and wherein the first set of maternal chromosomes is homozygous to the second set of maternal chromosomes can be produced. Also included is a method of determining the origin of the chromosomes with the use of a marker that is expressed during early seed development.

Provided is a method of obtaining a population of doubled haploid maize plants comprising the following steps: a) obtaining a set of haploid kernels by pollinating an ear with an inducer line wherein the ear comprises a set of maternal chromosomes and wherein the inducer line comprises a set of paternal chromosomes; b) contacting said set of haploid kernels with a medium comprising a doubling agent; c) electing a set of doubled haploid kernels wherein each kernel of said set of doubled haploid kernels comprises a triploid endosperm and a doubled haploid embryo; d) growing said set of doubled haploid kernels into a population of doubled haploid maize plants. The set of doubled haploid kernels produced have triploid endosperm and the triploid endosperm comprises two sets of maternal chromosomes and one set of paternal chromosomes. The doubled haploid embryo also has two sets of maternal chromosomes. These two sets of chromosomes are homozygous. The first set of chromosomes being replicated to form the second set of chromosomes. The various sets obtained from these methods can include the set of embryos on a maize ear, the set of kernels on a maize ear, and the set of maize doubled haploids plants.

Another aspect of the method is obtaining a doubled haploid maize plant comprising: a) pollinating silks of a maize ear with an inducer line; b) contacting the maize ear with a medium comprising a doubling agent; c) generating an embryo from the maize ear into a doubled haploid maize plant. Other aspects of the method include removing the maize ear from the plant with or without the stalk or some portion of the stalk attached. The ear can be removed before, during, or after pollination and placed into a solution. The ear can be placed in a solution 6 hours to 21 days after pollination and up to 35 days after pollination. The solution may comprise water or water and nutrients. The solution may come into contact with the ear directly or indirectly, for example via filter paper or cotton. The doubling agent can come in contact with the ear after pollination and before or after the ear is removed from the plant. The chromosomal doubling agent may come into contact with the ear directly or indirectly, for example via filter paper or cotton.

Another method provided is obtaining a set of doubled haploid maize embryos comprising the following steps: a) obtaining a set of haploid embryos by pollinating an ear with an inducer line; wherein the ear comprises a set of maternal chromosomes from an F1 maize plant; and wherein the inducer line comprises a set of paternal chromosomes; b) contacting said set of haploid embryos with a medium comprising a doubling agent; c) selecting a set of doubled haploid maize embryos wherein each doubled haploid maize embryo of said set of doubled haploid maize embryos is genetically different from each of the other doubled haploid maize embryos of said set of doubled haploid maize embryos; d) growing said set of doubled haploid maize embryos into a population of doubled haploid maize plants. This method develops a unique set of doubled haploid maize embryos. This unique set of embryos is derived directly from one maize ear, wherein "being derived directly" indicates that a filial generation does not occur between development of the haploid embryos and the development of the set of doubled haploid embryos.

A method of inbred selection is provided comprising the following steps: a) cross pollinating two inbred maize plants; b) growing the F1 seed; c) pollinating the F1 plant with an inducer line to produce haploid embryos; d) contacting the haploid embryos with a chromosome doubling agent to produce doubled haploid embryos; e) generating doubled haploid plants; f) evaluating said doubled haploid plants for agronomic performance and combining ability. The development of haploids step may also be done at later generations, F2, F3, F4, etc. Producing haploids from later generations allows for additional opportunities for recombination.

The methods provided can include the use of embryo rescue. Embryo rescue is performed by contacting an embryo with a medium containing nutrients and generating a plant. Phytohormones may or may not be included in the embryo rescue medium.

Another method of obtaining a transgenic doubled haploid embryo may comprise isolating a haploid embryo, transforming the haploid embryo, placing the haploid embryo on a medium comprising a chromosome doubling agent and selecting a transgenic doubled haploid embryo.

In any of these methods markers may be used in this process to distinguish the haploid embryos from the embryos obtained from normal pollination (2N).

In any of these methods the chromosomes can be doubled at the immature embryo stage, at the mature seed stage, or anytime between pollination of the plant and before the germination of the haploid seed.

In any of these methods the haploid embryo that undergoes chromosomal doubling may be isolated, may be in the seed or kernel, may be in the kernel on a slice of cob, may be on the ear or spike, or the haploid embryo may be in the kernel which is on the ear and on the plant. The doubling agent may reach the haploid embryo while the ear is on the plant and the plant is intact. For example, the doubling agent may be contacted directly or indirectly with the haploid embryo. In some cases the doubling agent can be transported by the plant. The plant may be grown hydroponically and the doubling agent can be taken up through the roots of the plant and transported to the haploid embryo. The plant may start out being grown in soil or a growing medium and then transferred to a hydroponic solution where the doubling agent can be added. In another aspect of the method the plant may be grown in soil or a growing medium and then the doubling agent is added to the soil or growing medium so that it can be transported to the haploid embryo.

Methods for obtaining homozygous plants, plant cells, and seeds are provided. Also provided are methods for obtaining haploid embryos and seeds and methods for increasing chromosomal doubling. The methods comprise contacting haploid cells with a chromosome doubling agent. The methods also comprise crossing a selected plant and an inducer line to produce haploid embryos or seeds. Other methods comprise crossing a selected plant and an inducer line to produce a haploid cell, and treating the haploid cell with a chromosome doubling agent. The methods provide doubled haploid plant cells which can be generated into a plant containing homozygous genes.

The methods avoid time consuming selfing and crossing methods to obtain a homozygous trait of interest or an essentially homozygous plant. The presented methods can be used to produce doubled haploid populations that do not contain the residual heterozygosity of inbreds obtained though the traditional method of self pollination. The methods can be useful for functional genomics, such as knock-out analysis, functional analysis of recessive genes, gene replacement, homologous recombination, gene targeting, transgene stacking, and evaluating lethal versus non-lethal analysis of genes. With the previously known diploid systems, these analyses are very complicated and costly.

Haploid induction systems have been developed for various plants to produce haploid tissues, plants and seeds. The haploid induction system can produce haploid plants from any genotype by crossing a selected line (as female) with an inducer line. Such inducer lines for maize include Stock 6 (Coe, 1959, Am. Nat. 93:381-382; Sharkar and Coe, 1966, Genetics 54:453-464) RWS (Roeber and Geiger 2001, submitted to Crop Science), KEMS (Deimling, Roeber, and Geiger, 1997, Vortr. Pflanzenzuchtg 38:203-224), or KMS and ZMS (Chalyk, Bylich & Chebotar, 1994, MNL 68:47; Chalyk & Chebotar, 2000, Plant Breeding 119:363-364), and indeterminate gametophyte (ig) mutation (Kermicle 1969 Science 166:1422-1424). The disclosures of which are incorporated herein by reference.

Wide hybridization crosses can also be used to produce haploids. This method is sometimes referred to as the bulbosum method (Kasha and Kao, 1970, Nature 225:874-876). This method of haploid production occurs due to the elimination of the chromosomes from the pollinating parent.

Methods for obtaining haploid plants are also disclosed in Kobayashi, M. et al., J. of Heredity 71(1):9-14, 1980, Pollacsek, M., Agronomie (Paris) 12(3):247-251, 1992; Cho-Un-Haing et al., J. of Plant Biol., 1996, 39(3):185-188; Verdoodt, L., et al., Feb. 1998, 96(2):294-300; Genetic Manipulation in Plant Breeding, Proceedings International Symposium Organized by EUCARPIA, Sep. 8-13, 1985, Berlin, Germany; Chalyk et al., 1994, Maize Genet Coop. Newsletter 68:47; Chalyk, S. T., 1999, Maize Genet. Coop. Newsletter 73:53-54; Coe, R. H., 1959, Am. Nat. 93:381-382; Deimling, S. et al., 1997, Vortr. Pflanzenzuchtg 38:203-204; Kato, A., 1999, J. Hered. 90:276-280; Lashermes, P. et al., 1988, Theor. Appl. Genet. 76:570-572 and 76:405-410; Tyrnov, V. S. et al., 1984, Dokl. Akad. Nauk. SSSR 276:735-738; Zabirova, E. R. et al., 1996, Kukuruza I Sorgo N4, 17-19; Aman, M. A., 1978, Indian J. Genet Plant Breed 38:452-457; Chalyk S. T., 1994, Euphytica 79:13-18; Chase, S. S., 1952, Agron. J. 44:263-267; Coe, E. H., 1959, Am. Nat. 93:381-382; Coe, E. H., and Sarkar, K. R., 1964 J. Hered. 55:231-233; Greenblatt, I. M. and Bock, M., 1967, J. Hered. 58:9-13; Kato, A., 1990, Maize Genet. Coop. Newsletter 65:109-110; Kato, A., 1997, Sex. Plant Reprod. 10:96-100; Nanda, D. K. and Chase, S. S., 1966, Crop Sci. 6:213-215; Sarkar, K. R. and Coe, E. H., 1966, Genetics 54:453-464; Sarkar, K. R. and Coe, E. H., 1971, Crop Sci. 11:543-544; Sarkar, K. R. and Sachan J. K. S., 1972, Indian J. Agric. Sci. 42:781-786; Kermicle J. L., 1969, Mehta Yeshwant, M. R., Genetics and Molecular Biology, September 2000, 23(3):617-622; Tahir, M. S. et al. Pakistan Journal of Scientific and Industrial Research, August 2000, 43(4):258-261; Knox, R. E. et al. Plant Breeding, August 2000, 119(4):289-298; and U.S. Pat. No. 5,639,951 the disclosures of which are incorporate herein by reference.

When an inducer line is used to pollinate a diploid plant, haploid embryos are derived. One sperm nucleus from the pollen fuses with the polar nuclei in the embryo sac to create a triploid (3N) endosperm. The triploid endosperm will contain 2 sets of chromosomes from the female and 1 set of chromosomes from the male, which in this case is the inducer line. The haploid embryo contains a single set of chromosomes, which are derived from the female plant.

Haploid cells, haploid embryos, haploid seeds, haploid seedlings or haploid plants can be treated with a chromosome doubling agent. Homozygous plants can be regenerated from haploid cells by contacting the haploid cells, such as haploid embryo cells, with chromosome doubling agents. The haploid cells may come in contact with the doubling agent at the time of pollination, anytime after pollination, typically 6 hours to 21 days after pollination, 6 hours to 15 days after pollination, at the mature seed stage, at the seedling stage, or at the plant stage. The haploid embryo may come in contact with the doubling agent when one sperm nucleus from a pollen grain fuses with the polar nuclei in the embryo sac to create a triploid (3N) endosperm (when the haploid embryo is formed), anytime after the pollination, typically 6 hours to 21 days after pollination, 6 hours to 15 days after pollination, or at the mature seed stage. The haploid embryo may be isolated. It may be contained within the kernel, ovule, or seed. It may also be on the ear in the case of corn, or on the spike as in the case of other grains such as wheat. The ear comprising the haploid embryo may be on the plant or isolated from the plant. The ear also may be sectioned. After chromosome doubling, the doubled haploid embryo will contain 2 copies of maternally derived chromosomes. The efficiency of the process for obtaining doubled haploid plants from haploid embryos may be greater than 10%, 20%, 30%, 50%, 60%, 70%, 80%, or 90%.

Methods of chromosome doubling are disclosed in Antoine-Michard, S. et al., Plant cell, tissue organ cult., Cordrecht, the Netherlands, Kluwer Academic Publishers, 1997, 48(3): 203-207; Kato, A., Maize Genetics Cooperation Newsletter 1997, 36-37; and Wan, Y. et al., TAG, 1989, 77: 889-892. Wan, Y. et al., TAG, 1991, 81: 205-211. The disclosures of which are incorporated herein by reference. Typical methods involve contacting the cells with colchicine, anti-microtubule agents or anti-microtubule herbicides, pronamide, nitrous oxide, or any mitotic inhibitor to create homozygous doubled haploid cells. The amount of colchicine used in medium is generally 0.01%-0.2% or approximately 0.05% or APM (5-225 µM). The amount of colchicines can range from approximately 400-600 mg/L or approximately 500 mg/L. The amount of pronamide in medium is approximately 0.5-20 µM. Examples of known mitotic inhibitors are included in Table 1. Other agents may be used with the mitotic inhibitors to improve doubling efficiency. Such agents may be dimethyl sulfoxide (DMSO), adjuvants, surfactants, and the like.

TABLE 1

| Common Name/ Trade name | CAS | IUPAC |
|---|---|---|
| Colchicine and Colchicine Derivatives | | |
| colchicine/ acetyltrimethylcolchicinic acid colchicine derivatives | | (S)—N-(5,6,7,9-tetrahydro-1,2,3,10-tetramethoxy-9-oxobenzo (a) heptalen-7-yl) acetamide |
| Carbamates | | |
| Carbetamide | (R)-1-(ethylcarbamoyl)ethyl carbanilate | (2R)—N-ethyl-2-[[(phenylamino)carbonyl]oxy]propanamide |
| chloropropham propham | | |
| Benzamides | | |
| Pronamide/ propyzamide tebutam | 3,5-dichloro-N-(1,1-dimethylpropynyl)benzamide | 3,5-dichloro-N-(1,1-dimethyl-2-propynyl)benzamide |
| Benzoic Acids | | |
| Chlorthal dimethyl (DCPA), Dicamba/dianat/ disugran (dicamba-methyl) (BANVEL, | 3,6-dichloro-o-anisic acid | 3,6-dichloro-2-methoxybenzoic acid |

TABLE 1-continued

| Common Name/ Trade name | CAS | IUPAC |
|---|---|---|
| CLARITY) | | |
| Dinitroaniline chromosome doubling agents | | |
| benfluralin/benefin/ (BALAN) | N-butyl-N-ethyl-α,α,α-trifluoro-2,6-dinitro-p-toluidine | N-butyl-N-ethyl-2,6-dinitro-4-(trifluoromethyl)benzenamine |
| butralin | (RS)—N-sec-butyl-4-tert-butyl-2,6-dinitroaniline | 4-(1,1-dimethylethyl)-N-(1-methylpropyl)-2,6-dinitrobenzenamine |
| chloralin | | |
| dinitramine | N1,N1-diethyl-2,6-dinitro-4-trifluoromethyl-m-phenylenediamine | N3,N3-diethyl-2,4-dinitro-6-(trifluoromethyl)-1,3-benzenediamine |
| ethalfluralin (Sonalan) | N-ethyl-α,α,α-trifluoro-N-(2-methylallyl)-2,6-dinitro-p-toluidine | N-ethyl-N-(2-methyl-2-propenyl)-2,6-dinitro-4-(trifluoromethyl)benzenamine |
| fluchloralin | N-(2-chloroethyl)-2,6-dinitro-N-propyl-4-(trifluoromethyl)aniline or N-(2-chloroethyl)-α,α,α-trifluoro-2,6-dinitro-N-propyl-p-toluidine | N-(2-chloroethyl)-2,6-dinitro-N-propyl-4-(trifluoromethyl)benzenamine |
| isopropalin | 4-isopropyl-2,6-dinitro-N,N-dipropylaniline | 4-(1-methylethyl)-2,6-dinitro-N,N-dipropylbenzenamine |
| methalpropalin | α,α,α-trifluoro-N-(2-methylallyl)-2,6-dinitro-N-propyl-p-toluidine | N-(2-methyl-2-propenyl)-2,6-dinitro-N-propyl-4-(trifluoromethyl)benzenamine |
| nitralin | 4-methylsulfonyl-2,6-dinitro-N,N-dipropylaniline | 4-(methylsulfonyl)-2,6-dinitro-N,N-dipropylbenzenamine |
| oryzalin (SURFLAN) | 3,5-dinitro-N4,N4-dipropylsulfanilamide | 4-(dipropylamino)-3,5-dinitrobenzenesulfonamide |
| pendimethalin (PROWL) | N-(1-ethylpropyl)-2,6-dinitro-3,4-xylidine | N-(1-ethylpropyl)-3,4-dimethyl-2,6-dinitrobenzenamine |
| prodiamine | 5-dipropylamino-α,α,α-trifluoro-4,6-dinitro-o-toluidine or 2,6-dinitro-N1,N1-dipropyl-4-trifluoromethyl-m-phenylenediamine | 2,4-dinitro-N3,N3-dipropyl-6-(trifluoromethyl)-1,3-benzenediamine |
| profluralin | N-cyclopropylmethyl-α,α,α-trifluoro-2,6-dinitro-N-propyl-p-toluidine or N-cyclopropylmethyl-2,6-dinitro-N-propyl-4-trifluoromethylaniline | N-(cyclopropylmethyl)-2,6-dinitro-N-propyl-4-(trifluoromethyl)benzenamine |
| trifluralin (TREFLAN, TRIFIC, TRILLIN) | α,α,α-trifluoro-2,6-dinitro-N,N-dipropyl-p-toluidine | 2,6-dinitro-N,N-dipropyl-4-(trifluoromethyl)benzenamine |
| Phosphoroamidates | | |
| AMP (Amiprofos methyl); amiprophos-methyl | | |
| Butamifos | O-ethyl O-6-nitro-m-tolyl (RS)-sec-butylphosphoramidothioate | O-ethyl O-(5-methyl-2-nitrophenyl) (1-methylpropyl)phosphoramidothioate |
| Pyridines | | |
| Dithiopyr | | |
| Thiazopyr | methyl 2-difluoromethyl-5-(4,5-dihydro-1,3-thiazol-2-yl)-4-isobutyl-6-trifluoromethylnicotinate | methyl 2-(difluoromethyl)-5-(4,5-dihydro-2-thiazolyl)-4-(2-methylpropyl)-6-(trifluoromethyl)-3-pyridinecarboxylate |

The chromosome doubling agent may come in contact with the embryo at various times. If the embryo is isolated the doubling agent may come in contact immediately after isolation and before germination. If the embryo is contained within the seed, it may come in contact with the doubling agent anytime after pollination and before dry down. The embryo whether it is isolated or not may come in contact with the doubling agent any time between 6 hours after pollination and 21 days after pollination. The duration of contact between the chromosomal doubling agent may vary. Contact may be from less than 24 hours, for example 4-12 hours, to about a week. The duration of contact is generally from about 24 hours to 2 days.

Methods provided may or may not go through a callus formation stage. The haploid embryos may be placed on a "non-callus promoting medium. The term "non-callus promoting medium" refers to a medium that does not support proliferation of dedifferentiated masses of cells or tissue. A preferred "non-callus promoting medium" is used for embryo rescue, containing typical salt and vitamin formulations well known in the art. Such embryo rescue, or embryo culture, media contain little or no auxin [for review see Raghaven, V., 1966. Biol. Rev. 41:1-58]. Embryo maturation medium also represents another preferred "non-callus promoting medium". Embryo maturation medium is used to promote development of in vitro cultured embryos, preventing precocious germination, and typically contain standard salt/vitamin formulations (depending on the species), increased sugar levels and/or exogenously added abscisic acid, with little or no auxin. Another type of medium is used for shoot culture, or multiple shoot proliferation. This multiple-shoot medium can again contain little or reduced auxin, but instead contain elevated levels of cytokinin that promote meristem proliferation and growth.

An auxin is defined as an endogenous plant hormone such as indole acetic acid (IAA), derivatives of IAA such as indole-3-buteric acid, as well as compounds with auxin-like activity such as 2,4-D, picloram, dicamba, 3,4-D, 2,4,5-T and naphthalene acetic acid (NAA).

A cytokinin is defined as a naturally occurring plant hormone such as 2-isopentynel adenine (2iP), zeatin and hidydrozeatin, or a synthetic compound with cytokinin-like activity such as kinetin and BAP (beynzylaminopurine).

Polynucleotides or polypeptides involved in growth stimulation or cell cycle stimulation can be used to increase the frequency of haploid embryos produced per ear, increase the recovery of haploid plants, and/or stimulate chromosomal doubling efficiency. The growth stimulation polynucleotide can be provided by either the female or male parent. The growth stimulation polynucleotide or polypeptide can be provided by stable or transient transformation. Polynucleotides whose overexpression has been shown to stimulate the cell cycle include Cyclin A, Cyclin B, Cyclin C, Cyclin D, Cyclin E, Cyclin F, Cyclin G, and Cyclin H; Pin1; E2F; Cdc25; RepA and similar plant viral polynucleotides encoding replication-associated proteins. See U.S. Patent Publication No. 2002/0188965.

After successful doubling of the haploid chromosomes, it may be desirable to remove the above growth stimulation polynucleotides. This can be accomplished by using various methods of gene excision, such as with the use of recombination sites and recombinases.

A scorable marker gene can be used in the methods, for example colored markers in the endosperm or embryo may be utilized. Such markers include GUS (U.S. Pat. Nos. 5,599,670 and 5,432,081), GFP (U.S. Pat. Nos. 6,146,826; 5,491,084; and WO 97/41228), luciferase (U.S. Pat. No. 5,674,713 and Ow et al. 1986 Science 234 (4778) 856-859), YFP, CFP, CRC (Ludwig et al., 1990), coral reef proteins or anthocyanin genes such as A, C, R-nj, R1-scm alleles, R1-mb (marbled aleurone), R1-r:standard, R1-Randolph, R1-ch:Stadler, R1-d:Catspaw, R1-d:Arapaho, R1-nj, R1-nj:Cudu, R1-nj: Chase, R1-scm2, R1-sc:124, R1-sup-R1-suppressible, R1 K10-II; R1 r1-X1, R1-ch, R1-g, R1-lsk, R1-r, R1-sc122, R1-sc*5691, R1-sc:m122, R1-sc:m2, R1-scm:3, R1-sk:nc-2, R1-sk, R1-st. etc. and others known in the art. The disclosures of which are incorporated herein by reference.

In order for an anthocyanin marker to work in maize various alleles have to be taken into consideration. The production of anthocyanin pigments in maize tissues includes the products of both structural and regulatory genes. Structural genes, such as A1, A2, Bz1, Bz2 and C1, encode the biosynthetic enzymes of the pathway. The anthocyanin regulatory genes fall into two classes of transcription factors, C1/P11 and R1/B1, which interact to activate transcription of the structural genes.

More specifically, anthocyanin expression in the kernel requires a color-determining allele at the C1 locus, such as C1 or C1-S. C1-S is dominant to the wildtype (C1) allele and show enhanced pigmentation (Cone, K C, et al. 1986. Molecular analysis of the maize anthocyanin regulatory locus C1. Proc. Natl. Acad. Sci. 83:9631-9635; Scheffler, B., et al. 1994. Molecular analysis of C1 alleles in Zea mays defined regions involved in the expression of this regulatory gene. Mol. Gen. Genet. 242:40-48). Expression of C1 in turn is dependent on the Vp1 gene; Vp1 encodes a transcription factor that is involved in the expression of genes during seed maturation. The kernel specificity of C1 expression results because Vp1 expression is limited to the endosperm (aleurone) and embryo (Hattori T, et al. 1992. The Viviparous-1 gene and abscisic acid activate the C1 regulatory gene for anthocyanin biosynthesis during seed maturation in maize. Genes & Dev. 6:609-618).

In addition, anthocyanin expression in the maize kernel (endosperm and/or embryo) requires certain R1/B1 alleles. To be useful in haploid/diploid screening, an allele must confer color in both the endosperm (aleurone) and embryo. (Coe et al. 1988, The genetics of corn. pp. 81-258. In: Sprague G F, Dudley J W (eds) Corn and Corn Improvement, $3^{rd}$ ed. Amer. Soc. Agronomy, Madison) listed three types of alleles which confer color in both the aleurone and scutellum (embryo): R-nj, R-scm and B-peru.

Rnj is the most commonly used allele for haploid/diploid screening of mature seeds (Nanda and Chase, 1966. An embryo marker for detecting monoploids of maize (Zea mays L). Crop Sci. 6:213-215; Greenblatt and Bock, 1967. A commercially desirable procedure for detection of monoploids in maize. J. Hered. 58:9-13). As was mentioned regarding C1, R-nj expression levels have been shown to be correlated with parameters of kernel maturation (Alexander and Cross, 1983. Grain fill characteristics of early maize (Zea mays) strains selected for variable R-nj expression. Euphytica 32:839-844). More recently, R-scm2 has also been used (Kato A. 2002. Chromosome doubling of haploid maize seedlings using nitrous oxide gas at the flower primordial stage. Plant breeding 121:370-377; and Kato A. 2003. Chromosome doubling method. U.S. Patent Application 20030005479).

Some inducer lines already contain a color marker. For various reasons it may be desirable to express the marker gene in the embryo. In particular, it may be desirable to express the marker gene in the early stage of development, about 10 hours-15 days after pollination. If the marker is a transgene, using an appropriate promoter such as an oleosin or a Lecd promoter may be beneficial. Haploid embryos can then be distinguished from the normally pollinated embryos because the haploid embryos will not contain the marker gene.

Selectable, scorable, negative, positive markers can be used in the methods. Markers may be come through the female or male plant. The preferable method is to have the markers come through the male plant.

Haploid cells from embryos, seeds, plants, etc. can be identified by several methods, such as, by chromosomal counts, measuring the length of guard cells, or by use of a Flow Cytometer.

Molecular markers or quantitative PCR can be used to determine if a tissue or plant is made of doubled haploid cells or is made of diploid cells (cells obtained through normal pollination).

Transformation of the haploid embryo may also be used in the methods. The type of transformation is not critical to the methods; various methods of transformation are currently available. As newer methods are available to transform host cells they may be directly applied. Accordingly, a wide variety of methods have been developed to insert a DNA sequence into the genome of a host cell to obtain the transcription and/or translation of the sequence. Thus, any method that provides for efficient transformation/transfection may be employed.

Methods for transforming various host cells are disclosed in Klein et al. "Transformation of microbes, plants and animals by particle bombardment", Bio/Technol. New York, N.Y., Nature Publishing Company, March 1992, 10(3):286-291. Techniques for transforming a wide variety of higher plant species are well known and described in the technical, scientific, and patent literature. See, for example, Weising et al., Ann. Rev. Genet. 22:421-477 (1988).

For example, the DNA construct may be introduced directly into the genomic DNA of the plant cell using techniques such as electroporation, PEG-induced transfection, particle bombardment, silicon fiber delivery, or microinjection of plant cell protoplasts or embryogenic callus. See, e.g., Tomes et al., Direct DNA Transfer into Intact Plant Cells Via Microprojectile Bombardment. pp. 197-213 in Plant Cell, Tissue and Organ Culture, Fundamental Methods. eds. 0. L. Gamborg and G. C. Phillips. Springer-Verlag Berlin Heidelberg New York, 1995. The introduction of DNA constructs using polyethylene glycol precipitation is described in Paszkowski et al., Embo J. 3:2717-2722 (1984). Electroporation techniques are described in Fromm et al., Proc. Natl. Acad. Sci. 82:5824 (1985). Ballistic transformation techniques are described in Klein et al., Nature 327:70-73 (1987).

Alternatively, the DNA constructs may be combined with suitable T-DNA flanking regions and introduced into a *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-meditated transformation techniques are well described in the scientific literature. See, for example Horsch et al., Science 233:496-498 (1984), and Fraley et al., Proc. Natl. Acad. Sci. 80:4803 (1983). For instance, *Agrobacterium* transformation of maize is described in U.S. Pat. No. 5,981,840. *Agrobacterium* transformation of monocot is found in U.S. Pat. No. 5,591,616. *Agrobacterium* transformation of soybeans is described in U.S. Pat. No. 5,563,055.

Other methods of transformation include (1) *Agrobacterium rhizogenes*-induced transformation (see, e.g., Lichtenstein and Fuller In: Genetic Engineering, vol. 6, P W J Rigby, Ed., London, Academic Press, 1987; and Lichtenstein, C. P., and Draper, J. In: DNA Cloning, Vol. 11, D. M. Glover, Ed., Oxford, IRI Press, 1985), Application PCT/US87/02512 (WO 88/02405 published Apr. 7, 1988) describes the use of *A. rhizogenes* strain A4 and its Ri plasmid along with *A. tumefaciens* vectors pARC8 or pARC16 (2) liposome-induced DNA uptake (see, e.g., Freeman et al., Plant Cell Physiol. 25:1353, 1984), (3) the vortexing method (see, e.g., Kindle, Proc. Natl. Acad. Sci., USA 87:1228, (1990).

DNA can also be introduced into plants by direct DNA transfer into pollen as described by Zhou et al., Methods in Enzymology 101:433 (1983); D. Hess, Intern Rev. Cytol. 107:367 (1987); Luo et al., Plant Mol. Biol. Reporter, 6:165 (1988). Expression of polypeptide coding nucleic acids can be obtained by injection of the DNA into reproductive organs of a plant as described by Pena et al., Nature 325:274 (1987). Transformation can also be achieved through electroporation of foreign DNA into sperm cells then microinjecting the transformed sperm cells into isolated embryo sacs as described in U.S. Pat. No. 6,300,543 by Cass et al. DNA can also be injected directly into the cells of immature embryos and the rehydration of desiccated embryos as described by Neuhaus et al., Theor. Appl. Genet. 75:30 (1987); and Benbrook et al., in Proceedings Bio Expo 1986, Butterworth, Stoneham, Mass., pp. 27-54 (1986).

Transformed haploid embryos which are derived by any of the above transformation techniques can be cultured to regenerate a whole plant which possesses the transformed genotype. Such regeneration techniques are called embryo rescue. Embryo rescue media can comprise certain phytohormones and energy sources or just energy sources. The growth medium may also contain a selection agent such as a biocide and/or herbicide. This selection agent can be used to indicate a marker which has been introduced through the transformation process. For transformation and regeneration of maize see, Gordon-Kamm et al., The Plant Cell 2:603-618 (1990).

The methods provided can be practiced with any plant. Such plants include but are not limited to *Zea mays* (also identified as corn or maize), soybean, oilseed *Brassica*, alfalfa, rice, rye, sorghum, sunflower, tobacco, potato, peanuts, cotton, sweet potato, cassava, sugar beets, tomato, oats, barley, and wheat.

Generation of embryos into plants is well known in the art. Embryo rescue techniques can be used to generate immature doubled haploid embryos into plants (Recent Research Developments in Genetics & Breeding. Vol. 1, Part II, 287-308 2004). The disclosure of which is herein incorporated by reference.

The temperature at which the methods can be performed can vary. The methods provided can be practiced at any temperature that does not kill a plant cell or plant or from about 16 degrees Celsius to 32 degrees Celsius. Any or all or any combination of the various steps of the invention: embryo isolation, culturing, embryo cell doubling may be performed in the light or dark.

All publications and patent applications mentioned in this specification are herein incorporated by reference to the same extent as if each individual publication or patent application was specifically and individually indicated to be incorporated by reference.

The following examples are offered by way of illustration and not by way of limitation.

EXAMPLES

Example 1

Obtaining a Population of Double Haploid Maize Plants

Seeds from an F1 maize plant are planted and the resulting plants are used as female parent plants (pollen receivers). Seeds from haploid inducer lines, such as Stock 6, RWS, KEMS, KMS or ZMS, are planted and the resulting plants are used as male parent plants (pollen donors). The ears of the female parent plants are shoot-bagged before silk emergence. The silks of the ears on the plants of the female parent plants are pollinated with viable pollen grains collected from the anthers of the male parent plants (haploid inducer plants). This pollination is controlled by the method used regularly in maize breeding program to avoid any foreign pollen contamination. The pollination method results in the production of a frequency of about 5-12% of haploid embryos in each ear. At approximately 9-14 days after pollination, the immature ears are harvested. The ears are surface sterilized in 30% Clorox bleach plus 0.5% Micro detergent for 20 minutes, and rinsed two times with sterile water. The haploid embryos are isolated based on the identification of the visible marker gene in the inducer lines. For example, if the inducer contains a GFP gene or CRC gene driven by a promoter that allows the GFP or CRC gene expression in the embryos at the early developmental stage. Typical promoters that are useful include the maize oleosin promoter or maize Lecd promoter etc. The haploid produced by this system is a maternal haploid that has only one set of chromosomes from the female parent in the embryo cells and has 3 sets of chromosomes in the endosperm cells, two of them from female parent and one of them from male parent. If the inducer line has a visible marker gene, such as GFP or CRC, this marker gene will be included in the endosperm cells only, but not in the embryo cells in the haploid kernels. By using this kind of visible marker, haploid embryos without GFP or CRC expression can be easily identified from the embryos that with GFP or CRC expression.

The haploid maize embryos are isolated using a scalpel and placed on a medium containing colchicine. After approximately 24 hours the embryos are transferred onto a medium without colchicine and placed in the dark. These doubled haploid embryos will be a heterogenius population of homozygous embryos. After approximately 6-10 days plantlets can be transferred to a light culture room. Approximately 7-14 days later, plantlets are transferred to flats containing potting soil and grown for 1 week in a growth chamber, subsequently grown an additional 1-2 weeks in the greenhouse, then transferred to pots and grown to maturity. These plants will be a heterogeneous population of doubled haploid plants. These fertile doubled haploid maize plants can be selfed and evaluated for breeding purposes.

Example 2

Obtaining Doubled Haploid Maize Plants Through the Doubling of Chromosomes in Immature Embryos Methods A diploid maize plant, "A", was pollinated with a haploid inducer line containing GFP. Immature embryos were isolated at 12 days after pollination and the embryo size is ranged from 1.9-2.0 mm long. The diploid embryos, GFP expressing embryos, were discarded. The haploid embryos, based on the absence of the GFP marker expression, were cultured on a medium comprising MS salts, MS vitamins, thiamine, asparagine, BAP, sucrose, gelrite, and 0.05% colchicine with scutellum side up for 24 hours at 26 C in the dark. These embryos were then cultured scutellum side down for 6-10 days at 26 C in dark on a media that did not contain a doubling agent. This medium comprised MS salts, MS vitamins, myo-inositol, sucrose, and gelrite. The plantlets germinated from these treated embryos were transferred to a light culture room at 26 C for another 2-3 weeks until healthy plantlets with good roots developed. These plantlets were transferred to soil and grown in a regular greenhouse to maturation. The plants were self-pollinated and the mature seeds will be harvested. The harvested seed from each plant will be grown as an ear-row and the plants will examined for uniformity of the plant morphology within each ear-row.

| Results | | | | | |
|---|---|---|---|---|---|
| Ear | Total # of Embryos | Haploid Embryos | Plantlets Germinated | Plantlets to Greenhouse | Fully Fertile Plants |
| 1 | 71 | 3 | 3 | 2 | 2 |
| 2 | 60 | 7 | 5 | 5 | 4* |
| 3 | 101 | 9 | 8 | 8 | 8 |
| Sum | 232 | 19 (8.2%) | 16 (84.2%) | 15 | 14 (93.3%) |

*One plant in this group has a partial of the tassel shedding pollen.

Example 3

Obtaining Doubled Haploid Maize Plants

Methods

Two different diploid maize lines, "B" and "C", were pollinated with a haploid inducer line, containing homozygous GFP. Immature embryos were isolated at 11 days after pollination and embryo size ranged from 1.5-1.6 mm in length. The diploid embryos, embryos showing GFP expression, were discarded. The haploid embryos, embryos not expressing GFP, were cultured on a modified MS medium containing 5 uM pronamide with scutellum side up for 48 hours at 26 C in dark. After approximately 48 hours the embryos were transferred to a modified MS medium without any doubling agent. Embryos were placed with scutellum side down for 6-10 days at 26 C in the dark. The plantlets germinated from these treated embryos were then moved into a light culture room at 26 C for another 3 weeks till healthy plantlets with good roots developed. These plantlets were then transferred to soil and grown in a regular greenhouse to maturation. The plants were self-pollinated and the mature seeds will be harvested. The harvested seed will be planted as an ear-row. The plants within a row will be examined for uniformity of the plant morphology.

| Results | | | | | |
|---|---|---|---|---|---|
| Line | Total Embryo | Haploid Embryo | Plantlet Germinated | Plantlet to Greenhouse | Fully Fertile Plant |
| B | 112 | 11 | 4 | 3 | 2* |
| C | 35 | 4 | 4 | 3 | 3 |
| Sum | 147 | 15 (10.2%) | 8 (53.3%) | 6 | 5 (83.3%) |

*One plant in this group has a part of the tassel shedding pollen.

Example 4

Doubled Haploid Seeds and Doubled Haploid Lines Derived from the Doubling of Chromosomes in Immature Embryos Doubled haploid seeds are obtained through the methods described in Examples 1, 2 and 3. The doubled haploid plants in example 1, 2 and 3 are self-pollinated and the doubled haploid seeds are formed on each doubled haploid plant. The seeds produced on each ear are homozygous seeds. This table provides an example of seeds harvested from 10 of these doubled haploid plants.

| Plant number | Tassel fertility | Number of seeds produced |
| --- | --- | --- |
| 1 | Fully fertile | 99 |
| 2 | Fully fertile | 11 |
| 3 | Fully fertile | 245 |
| 4 | Fully fertile | 175 |
| 5 | Fully fertile | 97 |
| 6 | Fully fertile | 183 |
| 7 | Fully fertile | 188 |
| 8 | Fully fertile | 124 |
| 9 | Fully fertile | 154 |
| 10 | Fully fertile | 275 |

To verify the homozygosity of these doubled haploid lines produced through doubling the chromosomes at the immature embryo stage, the seeds produced from each of doubled haploid ears are planted as the ear-row in the field. The plants within each ear-row are evaluated for their phenotypes, such as, plant height, ear height, number of leaves, plant shape, tassel shape, number of branches of the tassel, anther color, silk color, flowering time, etc. All of this information is used to verify the uniformity of the plants within each ear-row. Through these evaluations, these doubled haploid lines are confirmed as homozygous. To further confirm the homozygosity of these doubled haploid lines, molecular marker technology is used.

Example 5

Description of Immature Ear Treatment for Haploid Doubling

A maize ear is pollinated with an inducer line that is homozygous for the R-nj marker gene. The ear is taken about 6 hours to 35 days after pollination by severing the plant above and below the ear. The lower end of the stalk is immersed into a large container of water. The ears are brought to a sterile hood in the lab. The stalk is cut several inches below the ear with a sterile knife. The lower third end of the ear is submerged in a 2.5% Chlorox (sodium hypochlorite) for 10 minutes. The whole surface of the ear and stalk are wiped with 70% ethanol or a 5% of Chlorox solution. The severed upper end of the stalk is sealed with sterile lanolin. The lower third of the ear is placed into sterile distilled water to rinse for 10 minutes. The ear is placed into a sterile 250 ml side-arm flask containing sterile medium comprising a doubling agent such as colchicin or pronamide. The container can be any that meets the need for small-scale or large-scale application. A sterile paper towel can be used to seal the gaps between the flask and the ear. The paper towel and the flask can be wrapped with parafilm in order to seal the container. The side-arm of the flask is connected by sterile tubing to a sterile burette or separated container to supply additional medium or to change to new medium. The flow of medium is controlled with a clamp on the tube. The ear is emerged in a liquid medium containing doubling agent for 10 to 48 hours and then cultured on the liquid medium without the doubling agent for rest of the time. The ear is cultured on the medium until kernel maturation. The ear is dried and seeds are harvested. The doubled haploid and haploid seeds are identified based on the marker. For example, when the R-nj marker comes in from the inducer line the resulting haploid and doubled haploid seeds will have a colorless embryo and colored endosperm. The seeds that undergo normal pollination would have colored endosperm and colored embryo. Plant the doubled haploid seeds and self-pollinate these plants to produce the next generation of seeds. Plant the seeds produced from these plants as ear-row. Check uniformity of each ear-row.

Example 6

Second Description of Immature Ear Treatment for Haploid

Hybrid maize plants were pollinated by haploid inducer plants. The ears with part of the stalks attached were harvested from the hybrid plants 4-6 days after pollination (embryo length less than 0.4 mm). The stalks were about 4-8 inches long on each side of where the ears were attached. The ears and the attached stalks are surface sterilized with 70% ethanol or 5% Chlorox. The lower ends of the stalks containing the ears were emerged into liquid medium containing MS medium, MS vitamins, sucrose, etc. and 5 uM Pronamide, 0.5% DMSO for one day at 26 C. Then the ears still contained on the stalks were moved to a fresh medium containing MS medium, MS vitamins, sucrose etc. without doubling agent to allow the embryos and kernels to develop. The embryos within the ear can be isolated at any time after doubling. Embryo rescue can then be used to germinate immature embryos into plants. The germinated plants were grown to examine fertility.

| Results | | | | | |
| --- | --- | --- | --- | --- | --- |
| Ear number | Ear/stalk harvest | Number of plants to greenhouse | Number of plants with fertile tassel | Number of plants with sterile tassel | % of plants with fertile tassel |
| 1 | 6 days after pollination | 24 | 16 | 8 | 67% |
| 2 | 6 days after pollination | 32 | 30 | 2 | 94% |
| 3 | 5 days after pollination | 20 | 14 | 6 | 70% |
| 4 | 4 days after pollination | 20 | 19 | 1 | 95% |
| Sum | | 96 | 79 | 17 | 82% |

Example 7

Description of Immature Ear Treatment for Haploid Doubling While the Ear is on the Plant A maize ear is pollinated with an inducer line. At about 6 hours to 35 days after pollination the plant is taken and the roots of the plant are immersed into a container of nutrient solution comprising a doubling agent. The roots of the plant are emerged in a liquid medium containing doubling agent for 10 to 48 hours and then moved to a new hydroponic nutrient solution for rest of the time. Examples of doubling agent include but are not limited to pronamide, carbetamide, oryzalin and colchicines. The ear is allowed to develop. The doubled haploid embryos can either be isolated anytime after the doubling treatment. Embryo rescue can be performed or the ear can be allowed to develop until kernel maturation. The ear is allowed to mature the seeds can be dried and seeds are harvested. The doubled haploid and haploid seeds can be identified based on the marker. For example, if the R-nj marker comes in from the inducer line the resulting haploid and doubled haploid seeds will have a colorless embryo and colored endosperm. The seeds that undergo normal pollination would have colored endosperm and colored embryo. Plant the doubled haploid seeds and self-pollinate these plants to produce the next generation of seeds. Plant the seeds produced from these plants as ear-row. Check uniformity of each ear-row.

Example 8

Description of Obtaining a Doubled-Haploid Plant through Shoot Induction

A haploid embryo is isolated 6-12 days after pollination. The haploid embryo is placed with the axis-side up on a medium comprising a chromosomal doubling agent for 24 to 48 hours. The doubled haploid embryo (or an excised explant containing the apical meristem) is then placed on a shoot proliferation medium (SP medium) with the axis-side up (scutellum side down). Shoot proliferation medium contains MS salts and vitamins with 2 mg/l 2-benzyladenine, 2% sucrose and 9 g/l TC agar (see Lowe et al., 1995, Biotechnology 13:677-682), but in addition to the elevated levels of cytokinin such SP media can contain low levels of auxins such as 2,4-D or IBA (as in Zhong et al., 1992, Planta 187: 483-489). After multiple shoots form on the SP medium, they are transferred to a shoot regeneration medium (also referred to as a shoot elongation medium), which consists of MS medium with an optimal level of cytokinin. For some genotypes, no cytokinin is optimal for shoot elongation, while for other genotypes some cytokinin is necessary (i.e. 10 mg/l zeatin). Once shoot regeneration has occurred, the shoots are transferred onto root initiation medium, for example a MS medium containing no auxins or cytokinins. If plantlets have difficulty forming roots in the absence of auxin, rooting is promoted by culture on MS (Murashige and Skoog) or SH (Shenk and Hildebrandt) medium with 1 mg/l NAA, or by nicking the base of the stem with a scalpel and dipping the shoots in a 1 mg/l NAA solution. Doubled haploid plantlets are then transferred to a growth chamber and finally transplanted into the greenhouse for growth to maturity and seed production. Seeds from the doubled haploid plants are grown and tested for homozygosity using analysis with molecular markers and phenotypic observations.

As an alternative to providing the doubling agent to the haploid embryo before culture, embryos or embryo-explants containing the apical meristem can be placed on SP medium, and once shoot proliferation has begun the multiple shoot culture can be exposed to a chromosome-doubling agent for 24-48 hours. The tissue is then transferred to fresh SP medium for continued meristem proliferation or can be moved onto root initiation medium.

Example 9

Testing Different Hybrids and Timing of Doubling Agent

A maternal-haploid-inducing maize line was used to pollinate 4 different hybrid plants. The immature embryos derived from these crosses were isolated and placed directly on embryo rescue medium containing 5 uM pronamide. Embryos were kept on the pronamide medium for approximately 36 or 48 hours before being transferred to new media without the doubling agent.

The plantlets germinated from these treated embryos were then transferred into tubes until healthy plantlets with good roots developed. These plantlets were then transferred to soil and grown in a regular greenhouse to maturation. The plants were self-pollinated and the mature seeds were harvested. Progeny from a sample of the double haploid plants was checked using 120 molecular markers and confirmed for homozygosity.

| Results | | | | | |
|---|---|---|---|---|---|
| Female genotype | Embryo age-Days After Pollination | No. of embryos excised | Embryo size (mm) | Duration of time on 5 uM Pronamide (hours) | # of Double Haploid Plants with Ears |
| Hybrid 1 | 11 | 100 | 2.5 | 36 | 1 |
| Hybrid 2 | 11 | 176 | 2.5-3 | 36 | 4 |
| Hybrid 1 | 12 | 300 | 2.5 | 36 | 1 |
| Hybrid 3 | 12 | 279 | 2.5-3 | 36 | 13 |
| Hybrid 4 | 12 | 322 | 2.5 | 36 | 2 |
| Hybrid 3 | 10 | 236 | 2 | 48 | 6 |
| Hybrid 4 | 10 | 144 | 2 | 48 | 3 |

What is claimed is:

1. A method of obtaining a doubled haploid maize plant, said method comprising:
    (a) pollinating silks of a maize ear with a maize inducer line to produce at least one diploid maize embryo and at least one haploid maize embryo;
    (b) isolating said haploid maize embryo between 4-21 days after step (a), wherein said at least one haploid maize embryo is distinguished from the diploid maize embryos via expression of a marker;
    (c) contacting said haploid maize embryo with a chromosome doubling agent to produce at least one doubled haploid maize embryo cell;
    (d) culturing said doubled haploid maize embryo cell on a non-callus promoting medium; and
    (e) generating a doubled haploid maize plant from said doubled haploid maize embryo cell.

2. The method of claim 1, wherein the maize inducer line contains a marker gene that is expressed in embryo tissue.

3. The method of claim 2, wherein said marker gene is R-nj.

4. The method of claim 2, wherein said marker gene is GFP.

5. The method of claim 2, wherein said marker gene is expressed 4 or more days after pollination.

6. The method of claim 2, wherein said marker gene expresses anthocyanin pigments.

7. The method of claim 1, wherein the haploid maize embryo of step (c) is 0.4 mm to 3 mm in length.

8. The method of claim 1, wherein the chromosome doubling agent comprises an anti-microtubule agent.

9. The method of claim 1, wherein said chromosomal doubling agent is selected from the group consisting of colchicine, pronamide, dithipyr, and trifluralin.

10. The method of claim 1, wherein in step (c) the haploid embryo is in contact with the doubling agent for 4 hours to 48 hours.

* * * * *